United States Patent
Dubut et al.

(10) Patent No.: US 10,479,757 B2
(45) Date of Patent: Nov. 19, 2019

(54) N,N-DIMETHYLAMINOETHYL ACRYLATE COMPOSITION STABILIZED IN RESPECT OF DISCOLORING EFFECTS

(71) Applicant: Arkema France, Colombes (FR)

(72) Inventors: Fanny Dubut, Metz (FR); Benoit Riflade, Bazas (FR); Sandra Maget, Carling (FR)

(73) Assignee: Arkema France, Colombes (FR)

(*) Notice: Subject to any disclaimer, the term of this patent is extended or adjusted under 35 U.S.C. 154(b) by 0 days.

(21) Appl. No.: 16/096,305

(22) PCT Filed: Apr. 24, 2017

(86) PCT No.: PCT/FR2017/050960
§ 371 (c)(1),
(2) Date: Oct. 25, 2018

(87) PCT Pub. No.: WO2017/187067
PCT Pub. Date: Nov. 2, 2017

(65) Prior Publication Data
US 2019/0135731 A1    May 9, 2019

(30) Foreign Application Priority Data
Apr. 28, 2016    (FR) ..................... 16 53798

(51) Int. Cl.
C07C 213/10    (2006.01)
C07C 213/08    (2006.01)
B01D 3/10    (2006.01)
B01D 3/14    (2006.01)
C07C 219/08    (2006.01)
C08K 5/08    (2006.01)
C08K 5/17    (2006.01)

(52) U.S. Cl.
CPC .............. *C07C 213/10* (2013.01); *B01D 3/10* (2013.01); *B01D 3/143* (2013.01); *C07C 213/08* (2013.01); *C07C 219/08* (2013.01); *C08K 5/08* (2013.01); *C08K 5/175* (2013.01)

(58) Field of Classification Search
CPC ........ B01D 3/10; B01D 3/143; C07C 213/08; C07C 213/10
See application file for complete search history.

(56) References Cited

U.S. PATENT DOCUMENTS

| 5,912,384 | A | 6/1999 | Nagano |
| 6,376,703 | B1 | 4/2002 | Nagano |
| 6,437,173 | B1 | 8/2002 | Hurtel et al. |
| 7,294,240 | B2 | 11/2007 | Geisendoerfer et al. |
| 8,940,925 | B2 | 1/2015 | Paul et al. |
| 9,359,287 | B2 | 6/2016 | Paul et al. |
| 2004/0171868 | A1* | 9/2004 | Geisendoerfer ........ C07C 67/54 560/217 |

FOREIGN PATENT DOCUMENTS

FR    2 811 986    1/2002

* cited by examiner

Primary Examiner — Deborah D Carr
(74) Attorney, Agent, or Firm — Lynn B. Morreale

(57) ABSTRACT

The invention relates to the use of 2,6,-di-tert-butyl-4-methylphenol at a moiety of 25 to 200 ppm for stabilizing N,N-dimethylaminoethyl acrylate in respect of discoloring effects. The invention also relates to an N,N-dimethylaminoethyl acrylate stabilized in said manner and to a method for producing the same.

5 Claims, No Drawings

N,N-DIMETHYLAMINOETHYL ACRYLATE COMPOSITION STABILIZED IN RESPECT OF DISCOLORING EFFECTS

CROSS-REFERENCE TO RELATED APPLICATIONS

This application is a national stage application under 35 U.S.C. § 371 of PCT/FR2017/050960, filed Apr. 24, 2017 which claims benefit to application FR1653798, filed Apr. 28, 2016.

TECHNICAL FIELD

The present invention relates to the production N,N-dimethylaminoethyl acrylate by transesterification reaction of an alkyl acrylate such as methyl acrylate or ethyl acrylate, by N,N-dimethylaminoethanol, and the subject is more particularly the stabilization of N,N-dimethylaminoethyl acrylate with respect to coloration, by 2,6-di-tert-butyl-4-methylphenol.

PRIOR ART AND TECHNICAL PROBLEM

N,N-dimethylaminoethyl acrylate (hereinafter designated DMAEA) corresponding to the formula (I):

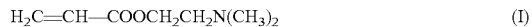

$$H_2C=CH-COOCH_2CH_2N(CH_3)_2 \quad (I)$$

is obtained by transesterification reaction between a light alkyl acrylate (also referred to as light acrylate) of formula (II): $CH_2=CH-COOR_1$, in which $R_1$ represents the methyl or ethyl radical, and N,N-dimethylaminoethanol (DMAE), according to the following reaction scheme:

$$CH_2=CH-COOR_1+HO-CH_2CH_2N(CH_3)_2 \Leftrightarrow DMAEA+R_1OH \quad (1)$$

The reaction is generally carried out in the presence of an excess of light alkyl acrylate and the reaction is shifted in the direction of the formation of DMAEA by distilling the light alcohol $R_1OH$ in the form of a light acrylate/$R_1OH$ alcohol azeotrope. The reaction is accompanied by side reactions producing impurities in the reaction medium. The reaction medium is subsequently subjected to a set of treatments with the aim of separating the pure product.

N,N-dimethylaminoethyl acrylate (DMAEA) and more generally dialkylaminoalkyl (meth)acrylates are starting materials for the preparation of quaternary salts for obtaining cationic polymers, of use as flocculants in the field of water treatment, as paper or textile treatment agents or in the field of mining operations and in the oil and gas industry.

The lack of stability over time under some conditions (temperature conditions, for example) of these compounds, especially the yellowing thereof, is problematic. This is because the preparation of quaternary salts from these starting materials may lead to randomly colored aqueous solutions and to the formation of colored cationic polymers which may be problematic in terms of coloring the water when they are subsequently used in water treatment.

In order to solve, or at least mask, this problem of color instability, DMAEA needs to be stored under certain temperature conditions, in particular at a temperature of less than 5° C. and in darkness, thereby complicating facilities for storing or transporting the product. In the absence of taking these precautions for storage, DMAEA is used quickly after production thereof, to avoid problems caused by the possible change in the coloration thereof.

The studies carried out in the prior art regarding the production of DMAEA were essentially conducted with the aim of obtaining a finished product of high purity.

By way of example, document EP 0960 877A2 describes a process for treating a reaction medium obtained by transesterification of ethyl acrylate (EA) and dimethylaminoethanol (DMAE) in the presence of a catalyst based on alkyl titanate. This process is based on a tailing operation (elimination of the catalyst and the heavy by-products) followed by a topping operation (elimination of the light compounds) and a final rectification, leading to a finished product of high purity, comprising less than 100 ppm of EA and less than 300 ppm of DMAE.

In the process described in document FR 2 811 986, it was proposed to use tetraethyl titanate in solution in DMAE as catalyst, in order additionally to avoid the impurities generated by the catalyst.

Other studies related to the optimization of the process for producing DMAEA, enabling the azeotropic fraction generated during the transesterification reaction to be recycled after purification on a unit for producing alkyl acrylate (WO 2010/086547), or to the reclamation of valuable products recovered from the heat treatment of the heavy, by-products formed during the process (WO 2013/045786).

The problem of stabilizing (meth)acrylic derivatives, in particular DMAEA, due to their ability to polymerize, is solved by using polymerization inhibitors introduced during the production or purification processes thereof. Regarding the problem of the change in color of DMAEA over time, it was proposed in patent EP 0850 916 to add at least one compound selected from compounds containing an amido group, esters of phosphorous acid, esters of phosphoric acid and phosphines, and at least one substituted phenolic compound. The examples show that the presence of the two compounds is necessary in order to guarantee the stabilization of DMAEA.

The aim of the present invention is therefore to provide a method better suited to an industrial context, for stabilizing DMAEA with respect to the coloration thereof, and therefore to guarantee the stability thereof with respect to coloration during storage.

The inventors have discovered, surprisingly, that the addition under certain conditions of the compound 2,6-di-tert-butyl-4-methylphenol made it possible to obtain a DMAEA that is stabilized with respect to coloration, independent of the conditions for synthesis or purification of the product.

2,6-di-tert-butyl-4-methylphenol (also referred to as 2,6-di-tert-butyl-p-cresol) is a compound belonging to the polymerization inhibitors of use in processes for producing and purifying (meth)acrylic derivatives, like phenothiazine, hydroquinone, hydroquinone methyl ether, tert-butyl catechol or the TEMPO nitroxyl compounds.

For example, in the process for synthesizing (meth)acrylic esters described in U.S. Pat. No. 7,294,240, approximately 10-20 ppm of hydroquinone methyl ether or 2,6-di-tert-butyl-p-cresol are introduced at the point of drawing off the purified (meth)acrylic ester from the side, in order to stabilize the desired product. In the process described in document US 2004/171868, the (meth)acrylic ester produced is storage-stabilized by addition of a stabilizing agent, preferably selected from 2,6-di-tert-butyl-p-cresol and hydroquinone methyl ether at a content which may range from 5 to 500 ppm. However, the effect of the 2,6-di-tert-butyl-4-methylphenol alone on the inhibition of coloration of DMAEA is not described in these documents and has never been suggested in the prior art.

SUMMARY OF THE INVENTION

Therefore, the subject of the present invention is a composition of N,N-dimethylaminoethyl acrylate that is stabilized with respect to coloration, comprising from 25 to 200 ppm of 2,6-di-tert-butyl-4-methylphenol.

"Stabilized with respect to coloration" is intended to mean that the change in coloration is at least twice as slow in the presence of 2,6-di-tert-butyl-4-methylphenol as in the absence of 2,6-di-tert-butyl-4-methylphenol when the composition is stored at a temperature ranging from 0 to 40° C. for a duration which may range from at least 10 days up to 30 days in darkness.

According to one embodiment, the stabilized composition has a coloration of less than 100 Apha, preferably less than 30 Apha, more preferentially less than 20 Apha, determined by measuring the absorbance of the composition using a colorimeter. Preferably, the stabilized composition has a coloration of less than 20 Apha after storage at room temperature (approximately 20° C.) in darkness for a period of 30 days.

Another subject of the invention is a process for the continuous production of a composition of N,N-dimethylaminoethyl acrylate that is stabilized with respect to coloration, comprising a transesterification reaction between a light acrylate selected from methyl acrylate and ethyl acrylate, and dimethylaminoethanol in the presence of a catalyst, followed by a treatment for purification of the reaction mixture comprising a final distillation of the purified N,N-dimethylaminoethyl acrylate, characterized in that 25 to 200 ppm of 2,6-di-tert-butyl-4-methylphenol are introduced at the outlet of the distilled gaseous stream of purified N,N-dimethylaminoethyl acrylate, before condensation of the final product.

Another subject of the invention is the use of 2,6-di-tert-butyl-4-methylphenol at a content of between 25 and 200 ppm for stabilizing N,N-dimethylaminoethyl acrylate with respect to coloration.

Use is preferably made of ethyl acrylate as light acrylate for the transesterification reaction.

According to the invention, 2,6-di-tert-butyl-4-methylphenol introduced in small amounts at the end of the DMAEA purification process inhibits the change in coloration of the DMAEA, and thus enables longer storage of the product at higher temperatures than the temperature generally required; in particular, it enables storage at room temperature.

The invention is now described in greater detail and in a nonlimiting manner in the description which follows.

DETAILED DESCRIPTION OF THE INVENTION 2,6-di-tert-butyl-4-methylphenol (or 2,6-di-test-butyl-p-cresol or butylated hydroxytoluene) (referred to in the remainder of the document as BHT), of CAS number 128-37-0, is commercially available in the form of white crystalline powder.

According to the invention, the BHT present in the purified DMAEA at a content ranging from 25 to 200 ppm, preferably from 25 to 100 ppm, more preferentially from 30 to 80 ppm, more particularly from 30 to 50 ppm, leads to a composition that is stabilized with respect to coloration, of use as starting material for preparing polymers.

The BHT is introduced in unmodified form or in the form of a solution which may be prepared in DMAEA but also in the starting materials used for obtaining the DMAEA, such as the light alkyl acrylate or the heavy alcohol, in the presence of other stabilizers such as MEHQ.

The composition according to the invention may also comprise at least one stabilizer for inhibiting the polymerization of the DMAEA, selected for example from hydroquinone, hydroquinone methyl ether (MEHQ) or mixtures thereof at a content generally of between 200 ppm and 1000 ppm, preferably between 500 and 800 ppm. MEHQ is generally used as DMAEA polymerization inhibitor at a content of approximately 700 ppm. According to a preferred embodiment, the composition according to the invention comprises 800 ppm of MEHQ.

The composition also comprises residual impurities in small amounts.

The composition that is stabilized with respect to coloration according to the invention has a coloration of less than 100 Apha, preferably less than 30 Apha, more preferentially less than 20 Apha. The coloration of the composition is stabilized, that is to say that the change thereof is at least twice as slow due to the presence of BHT as in the absence of BHT when the composition is stored at a temperature ranging from 0 to 40° C. for a duration which may range from at least 10 days up to 30 days in darkness. The composition according to the invention may thus be stored in darkness at room temperature without the coloration thereof changing quickly. Advantageously, the composition according to the invention has a coloration of less than 20 Apha after storage at 20° C. in darkness for approximately 30 days.

The composition according to the invention is used for preparing cationic polymers of use as flocculants in the field of water treatment, as paper or textile treatment agents or in the field of mining operations and in the oil and gas industry.

Advantageously, the BHT is introduced continuously at the end of the DMAEA purification treatment, at the same time as the MEHQ, in particular into the final distillate of the purified product which is subsequently condensed in order to recover the stabilized composition of purified DMAEA.

The DMAEA purification treatment may be carried out in different ways, and employ different separation and/or extraction techniques well-known to those skilled in the art, in particular using distillation columns and/or film evaporators and/or condensers, decanters, etc.

More particularly, the purification process may comprise a tailing step (eliminating the heavy by-products and the catalyst) followed by a topping step (elimination of the light by-products), or conversely may comprise a topping step followed by a tailing step, optionally followed by a rectification. The purified product may be recovered by being drawn off from the side of the distillation column used for the final topping and/or tailing operation, or at the top of the final rectification column.

According to a particular embodiment, a process for the continuous production of a composition of N,N-dimethylaminoethyl acrylate that is stabilized with respect to coloration, as defined according to the invention may comprise the following steps:

a) a transesterification reaction is carried out between a light acrylate selected from methyl acrylate and ethyl acrylate, and dimethylaminoethanol in the presence of a transesterification catalyst and in the presence of at least one polymerization inhibitor, the corresponding azeotropic mixture of light acrylate/light alcohol being drawn off continuously during the reaction;

b) the crude reaction mixture is conveyed to a first distillation column C1, referred to as tailing column, under reduced pressure, the crude reaction mixture comprising the desired N,N-dimethylaminoethyl acrylate with, as light products, dimethylaminoethanol and unreacted light acrylate and, as heavy products, the catalyst, the polymerization inhibitor(s) and also heavy reaction by-products, making it possible to obtain:
  at the top, a stream composed essentially of N,N-dimethylaminoethyl acrylate and light products, comprising a minor fraction of heavy products but devoid, or substantially devoid, of catalyst; and
  at the bottom, a stream composed of heavy products with a minor fraction of N,N-dimethylaminoethyl acrylate and the catalyst; then
c) the top stream from the first distillation column C1 is conveyed to a second distillation column C2, referred to as topping column, under reduced pressure, making it possible to obtain:
  at the top, a stream composed of light products with a minor fraction of N,N-dimethylaminoethyl acrylate; and
  at the bottom, N,N-dimethylaminoethyl acrylate containing traces of light products, heavy reaction by-products and the polymerization inhibitor(s); then
d) the bottom stream from the second distillation column C2 is conveyed to a third distillation column C3, referred to as rectification column, under reduced pressure, into the top of which 25 to 200 ppm of 2,6-di-tert-butyl-4-methylphenol are introduced, making it possible to obtain:
  at the top, a gaseous stream of purified N,N-dimethylaminoethyl acrylate that is stabilized with respect to coloration which is subsequently condensed; and
  at the bottom, essentially the polymerization inhibitor(s).

It is clearly understood that the above process may comprise other preliminary, intermediate or subsequent steps, provided that they do not have a negative effect on obtaining the purified N,N-dimethylaminoethyl acrylate, or rather that they improve the productivity of the process.

The operating conditions for carrying out steps a) to d) of the process according to the invention, especially the reaction conditions or the distillation conditions, are those well-known to those skilled in the art, and may be those described in document EP 0960 877A2.

The examples below illustrate the present invention without however limiting the scope thereof.

EXAMPLES

The coloration of different samples of DMAEA containing BHT or not containing BHT was measured under different conditions using a LANGE LICO 400 colorimeter, relative to a 10 Apha standard.

Example 1 (According to the Invention)

A sample of DMAEA comprising 46 ppm of BHT was stored in darkness at 20° C. for 30 days.
The coloration of the sample was determined at t=0, after 10 days, after 20 days and after 30 days.
t=0: 8 Apha; t=10 days: 09 Apha; t=20 days: 12 Apha; t=30 days: 15 Apha Example 2 (Comparative)

A sample of DMAEA not comprising BHT was stored under the same conditions as those of example 1.
The coloration of the sample was determined at t=0, after 10 days, after 20 days and after 30 days.
t=0: 8 Apha; t=10 days: 23 Apha; t=20 days: 45 Apha; t=30 days: 72 Apha Example 3 (According to the Invention)

A sample of DMAEA comprising 46 ppm of BHT was stored in darkness at 30° C. for 30 days.
The coloration of the sample was determined at t=0, after 10 days, after 20 days and after 30 days.
t=0: 8 Apha; t=10 days: 26 Apha; t=20 days: 47 Apha; t=30 days: 82 Apha Example 4 (Comparative)

A sample of DMAEA not comprising BHT was stored under the same conditions as those of example 3.
The coloration of the sample was determined at 0, after 10 days, after 20 days and after 30 days.
t=0: 8 Apha; t=10 days: 55 Apha
t=20 days: >100 Apha; t=30 days: >200 Apha Example 5

The change in the coloration of a sample of DMAEA kept in darkness at 30° C. for a period ranging up to 30 days, without addition of BHT and in the presence of 10 ppm or 36 ppm of BHT, was monitored. The results assembled in Table 1 show that BHT added at a content of 10 ppm does not sufficiently stabilize the DMAEA which has coloration greater than 100 Apha after 30 days of storage.

TABLE 1

| BHT content, ppm | 0 | 10 | 36 |
|---|---|---|---|
| Coloration in Apha, t = 0 | 4 | 4 | 4 |
| 10 days | 40 | 26 | 12 |
| 20 days | 145 | 68 | 34 |
| 30 days | >350 | 135 | 45 |

Example 6 (Reference)

The teaching of document EP 0850916 was reproduced by measuring the coloration (Apha), after storing in darkness at 20° C. for approximately 30 days, of a sample of (commercial) DMAEA after addition of a phenolic compound (MEHQ or Topanol A) alone or in combination with a phosphorus-based compound (triphenylphosphine, Pph3). The contents are expressed in ppm.
The results are collated in Table 2 below.

TABLE 2

| | MEHQ | Topanol A | PPh$_3$ | Coloration t = 0 | Coloration 9 days | Coloration 23 days | Coloration 28 days |
|---|---|---|---|---|---|---|---|
| Test 1 | 121 | | | 10 | 14 | 40 | 56 |
| Test 2 | | 47 | | 4 | 8 | 33 | 45 |
| Test 3 | 1042 | | | 5 | 8 | 22 | 30 |
| Test 4 | 1014 | | 1000 | 5 | 7 | 8 | 9 |

The addition of a substituted phenolic compound such as MEHQ or Topanol A at a content of between 25 and 200 ppm does not make it possible to maintain the coloration of DMAEA after 30 days at a value as low as that obtained with the addition of 46 ppm of BHT (15 Apha) according to example 1 according to the invention.

The selection of the BHT corresponding to the formula of the phenolic compounds described in the prior art therefore leads to a surprising effect on the stabilization of DMAEA with respect to coloration.

The addition of a greater amount of MEHQ (more than 1000 ppm) alone does not make it possible to achieve the effect of BHT.

Test 4 confirms that the DMAEA is sufficiently stabilized by combining the phenolic derivative MEHQ with a phosphine compound.

The invention, based on the addition of solely BHT at a content of less than 200 ppm, thus provides a simpler and more economical solution to the problem of stabilizing DMAEA with respect to coloration than that of the prior art.

The invention claimed is:

1. A process for the continuous production of a composition of N,N-dimethylaminoethyl acrylate that is stabilized with respect to coloration, comprising from 25 to 200 ppm of 2,6-di-tert-butyl-4-methylphenol, said process comprising the steps of transesterifying a light acrylate selected from the group consisting of methyl acrylate and ethyl acrylate, with dimethylaminoethanol in the presence of a catalyst, followed by a treatment for purifying a reaction mixture comprising a final distillation of purified N,N-dimethylaminoethyl acrylate, wherein 25 to 200 ppm of 2,6-di-tert-butyl-4-methylphenol are introduced at an outlet of the distilled gaseous stream of purified N,N-dimethylaminoethyl acrylate, before condensation of final product.

2. The process of claim 1 comprising the following steps:
   a) transesterifying a light acrylate selected from the group consisting of methyl acrylate and ethyl acrylate, with dimethylaminoethanol in the presence of a transesterification catalyst and at least one polymerization inhibitor, a corresponding azeotropic mixture of light acrylate/light alcohol being drawn off continuously during the reaction;
   b) conveying a crude reaction mixture to a first distillation column C1, referred to as tailing column, under reduced pressure, the crude reaction mixture comprising the desired N,N-dimethylaminoethyl acrylate with, as light products, dimethylaminoethanol and unreacted light acrylate and, as heavy products, the catalyst, the polymerization inhibitor(s) and heavy reaction by-products, to obtain:
      at the top, a stream composed essentially of N,N-dimethylaminoethyl acrylate and light products, comprising a minor fraction of heavy products but devoid, or substantially devoid, of catalyst; and
      at the bottom, a stream composed of heavy products with a minor fraction of N,N-dimethylaminoethyl acrylate and the catalyst; then
   c) conveying the top stream from the first distillation column C1 to a second distillation column C2, referred to as topping column, under reduced pressure, to obtain:
      at the top, a stream composed of light products with a minor fraction of N,N-dimethylaminoethyl acrylate; and
      at the bottom, N,N-dimethylaminoethyl acrylate containing traces of light products, heavy reaction by-products and the polymerization inhibitor(s); then
   d) conveying the bottom stream from the second distillation column C2 to a third distillation column C3, referred to as rectification column, under reduced pressure, into the top of which 25 to 200 ppm of 2,6-di-tert-butyl-4-methylphenol is introduced, to obtain:
      at the top, a gaseous stream of purified N,N-dimethylaminoethyl acrylate that is stabilized with respect to coloration which is subsequently condensed; and
      at the bottom, a stream consisting essentially of the polymerization inhibitor(s).

3. The process as claimed in claim 1 wherein the light acrylate is ethyl acrylate.

4. The process of claim 1 wherein the composition has a coloration of less than 100.

5. The process of claim 1 wherein the composition further comprises at least one polymerization inhibitor, selected from the group consisting of hydroquinone, hydroquinone methyl ether (MEHQ) and mixtures thereof.

* * * * *